United States Patent [19]

Wright

[11] Patent Number: 5,056,534
[45] Date of Patent: Oct. 15, 1991

[54] SNORE INHIBITING DEVICE

[76] Inventor: David W. R. Wright, 20 Cross Road, Myrtle Bank, South Australia, 5064, Australia

[21] Appl. No.: 519,257

[22] Filed: May 2, 1990

Related U.S. Application Data

[63] Continuation of Ser. No. 215,643, Jul. 6, 1988, abandoned.

[30] Foreign Application Priority Data

Jul. 8, 1987 [AU] Australia ................. PI2979

[51] Int. Cl.$^5$ ................................ A61F 5/56
[52] U.S. Cl. .................... 128/848; 128/862; 433/146
[58] Field of Search ............... 128/848, 859, 861, 862; 433/146

[56] References Cited

U.S. PATENT DOCUMENTS

| | | | |
|---|---|---|---|
| 2,505,056 | 4/1950 | Messine | 128/12 |
| 2,528,370 | 10/1950 | Johnston | 128/136 |
| 2,531,222 | 11/1950 | Kesling | 32/14 |
| 2,604,093 | 7/1952 | Orth | 128/136 |
| 2,705,006 | 3/1955 | Celtel et al. | 128/848 |
| 2,800,898 | 7/1957 | Greenblum | 128/136 |
| 2,827,899 | 3/1958 | Altieri | 128/862 |
| 3,132,647 | 5/1964 | Corniello | 128/136 |
| 3,211,143 | 10/1965 | Grossberg | 128/136 |
| 3,286,576 | 11/1966 | West | 128/859 |
| 3,434,470 | 3/1969 | Strickland | 128/136 |
| 3,448,738 | 6/1969 | Gerghash | 128/136 |
| 3,457,916 | 7/1969 | Wolicki | 128/862 |
| 4,169,473 | 10/1979 | Samelson | 128/136 |
| 4,196,724 | 4/1980 | Wirt et al. | 128/136 |
| 4,304,227 | 12/1981 | Samelson | 128/136 |
| 4,569,342 | 2/1986 | von Nostitz | 128/862 |

FOREIGN PATENT DOCUMENTS

| | | | |
|---|---|---|---|
| 480423 | 8/1929 | Fed. Rep. of Germany | 128/861 |
| 1569129 | 6/1980 | United Kingdom | 128/862 |

Primary Examiner—Randall L. Green
Assistant Examiner—K. Reichle
Attorney, Agent, or Firm—Brown, Martin, Haller & McClain

[57] ABSTRACT

A snore inhibiting device comprises a moulding of resilient yieldable material formed to be complementary to the shape of the teeth of the upper arch of a user, so as to have a plurality of interconnected pockets to closely engage the teeth of the upper arch, and also having a depending flange which is co-operable with the lower lip of a user, so as to obstruct the air flow passage through the mouth to the lungs, the depth of the flange being such that the passage opens upon wide opening of the mouth, and is such that the mouth can be closed with comfort.

4 Claims, 1 Drawing Sheet

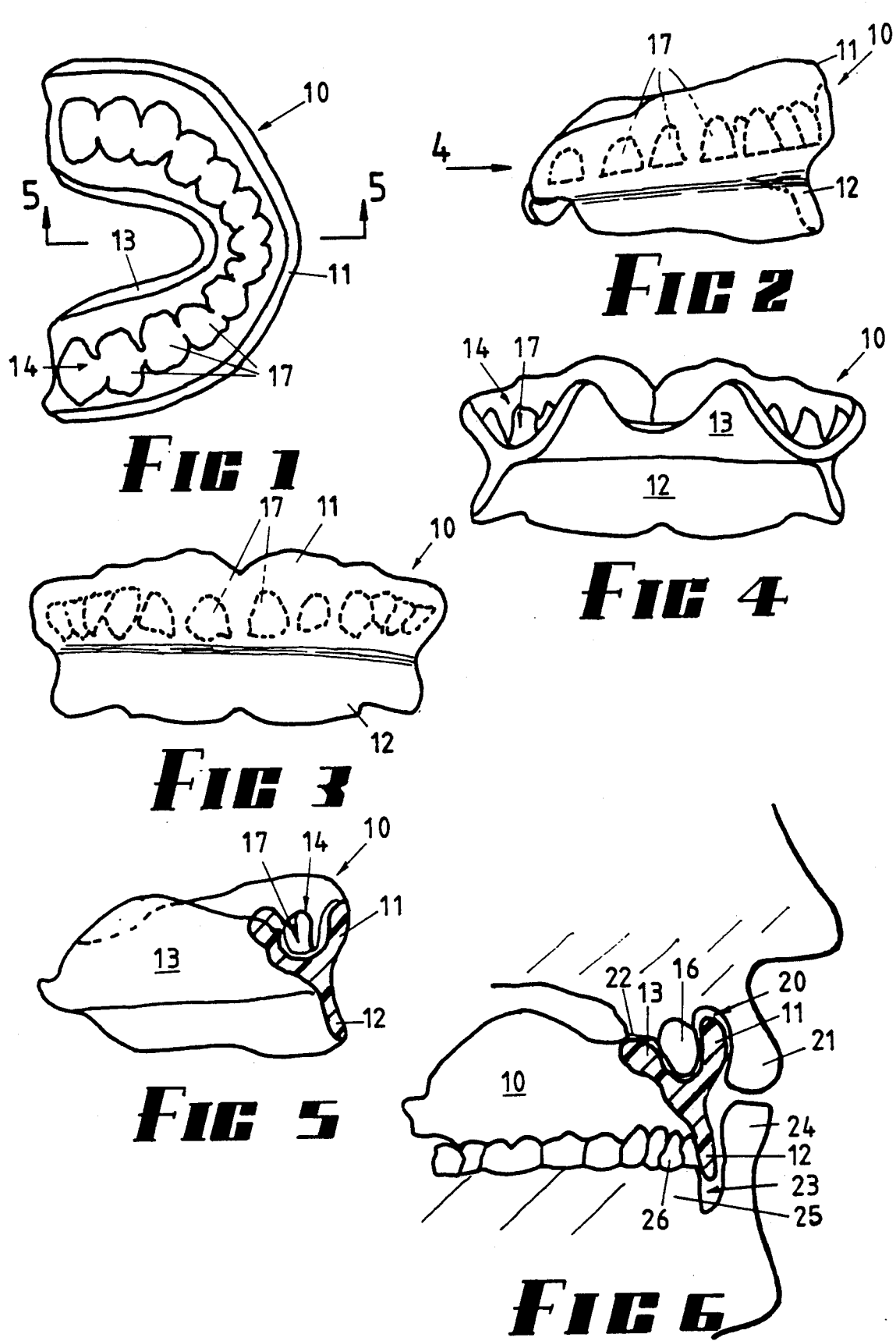

SNORE INHIBITING DEVICE

This is a continuation of application Ser. No. 215,643, filed July 6, 1988, now abandoned.

This invention relates to an oral device for insertion into the mouth for inhibition of snoring.

PRIOR ART

The prior art known to the applicant comprises the related U.S. Pat. Nos. 4,169,473 and 4,304,227 in the name of Samelson, 3,132,647 to Corniello, and 3,434,470 to Strickland. Other known prior art does not contribute further, but includes: U.S. Pat. Nos. 4,196,724 to Wirt; 3,448,738 to Berghash; 3,211,143 to Grossberg; 2,800,898 to Greenblum; 2,604,093 to Orth; 2,531,222 to Kesling; 2,528,370 to Johnston; and 2,505,056 Messine.

The closest prior art of the three to the invention herein is probably that of Strickland, which illustrates a U-shaped channel adapted to be placed in the mouth, and having a structure which releasably grips the upper teeth. However the problem with a Strickland device is that it does not necessarily close the mouth against ingress of air, and it is the passage of air through the mouth which causes vibration of the uvula and soft palate. With the Strickland device, air can still pass the lower lip and the lower teeth and cause the unwanted vibration.

Another problem is that there is a tendency for any oral device placed in the mouth of a person when asleep to be dislodged, and it is the applicant's belief that the Strickland device would not be completely comfortable within the mouth since it partly bridges the intra-oral cavity, and, for comfort and retention, the device either has to be a very close accurate fit to the teeth, or retained thereto by some adhesive or mechanical means in order to avoid the possibility of dislodgement.

BACKGROUND OF THE INVENTION

One of the major problems encountered with oral devices is that, if uncomfortable, they will not be worn regularly by people who need their use. Therefore it is believed that the very large and cumbersome arrangements shown in the other cited prior art is unlikely to be generally acceptable except in cases where patients are in most serious need of medical assistance.

For example, one would expect wearer resistance to devices such as Messine, U.S. Pat. No. 2,505,056, or Johnston, U.S. Pat. No. 2,528,370, on the grounds that discomfort is caused by some distortion or restriction of the jaw, and could result in loss of sleep. The H section device of Samelson, U.S. Pat. No. 4,304,227 and 4,169,473 would no doubt be effective, but is very bulky and can restrict free movement of the tongue.

One object of this invention is to provide a snore inhibiting device which is unlikely to be dislodged during sleep, and another object is to provide a device which, although comfortable, will very effectively restrict the flow of air into the mouth when used by a user, thereby causing the flow of air to the lungs to pass solely through the nose.

BRIEF SUMMARY OF THE INVENTION

In order to retain comfort for a user, there should be a minimum of obstruction in the intra-oral space of a user's mouth. To reduce likelihood of accidental displacement during sleep, the device should be positively located, ideally to the user's teeth. To prevent discomfort due to restriction of jaw movement, the device should however, preferably not be located on the lower arch. To inhibit air passage through the mouth, the device should normally obstruct the passage for most of its area. To enable a user to breathe additional air, the device should not obstruct the air passage upon involuntary wide opening of the mouth as can occur during sleep.

In this invention a snore inhibiting device comprises a moulding of resilient yieldable material formed to be complementary to the shape of the teeth of the upper arch of a user, so as to have a plurality of interconnected pockets to closely engage the teeth of the upper arch, and also having a depending flange which is co-operable with the lower lip of a user, so as to obstruct the air flow passage through the mouth to the lungs, the depth of the flange being such that the passage opens upon wide opening of the mouth, and is such that the mouth can be fully closed with comfort.

In almost all instances the material of the invention will be a soft yieldable material, although there are instances wherein a stiffer material may be required.

If a lower flange is thin and flexible, and depends into the recess between the lower gum and the lower lip of a user, the device will be less likely to be accidentally dislodged if the lower jaw moves in use. Further, if an upper flange extends between the upper gum and the upper lip, the dislodgement is still further inhibited, and again if the pockets are made complementary in shape to the upper teeth of a user, there will be little likelihood of dislodgement. Since the likelihood of dislodgement is substantially reduced, it is possible to make the walls of the three flanges of the device flexible, and therefore the device is comfortable for a user to insert in his mouth, and remain comfortable overnight.

More specifically, the invention consists of a snore inhibiting oral device comprising a heat deformable moulding which, in plan, comprises a general "U" shape and, in cross-section, three flanges defining a general "Y" shape, the size and shape of the device being such that, when moulded to the shape of and inserted in the mouth of a user, two of the flanges engage respectively front and rear surfaces of the teeth of one of the user's arches, and the third flange lies between the teeth of the other arch and a lip of the user.

BRIEF DESCRIPTION OF THE DRAWINGS

An embodiment of the invention is described hereunder in some detail with reference to, and is illustrated in, the accompanying drawings, in which:

FIG. 1 is a plan view of a snore inhibiting oral device;

FIG. 2 is a side elevation of FIG. 1;

FIG. 3 is a front elevation of FIG. 2;

FIG. 4 is a rear elevation (arrow 4) of FIG. 2;

FIG. 5 is a central section of FIG. 1 taken on line 5—5; and

FIG. 6 is a section corresponding to FIG. 5 but showing the oral device in the mouth of a user.

It is well known in the art that there are certain heat deformable substances which will soften with temperature, and will readily conform to the shape of the mouth at that temperature and retain that conformation when cooled, so that for example a mouth guard of ethylene vinyl acetate copolymer can be formed by heating in hot water, placing in the mouth, closing the jaws, removing the mouth guard and quickly chilling, and thereafter the mouth guard will fit the surfaces within the mouth. This invention seeks to make use of this technique. Alternatively, the invention seeks to make use of this property of the material to adapt the device to a stone model replica of the patient's teeth and gums, in instances wherein a very accurately fitting custom-made device is required, without placing heated material in the patient's mouth.

In the illustrated embodiment of the invention, an oral snore inhibiting device 10 has a generally Y-shaped cross-sectional shape, as illustrated in section in FIGS. 5 and 6. It comprises an upper flange 11, a lower flange 12 and an inner flange 13. As shown in plan in FIG. 1, the device is generally U-shaped, and the upper and inner flanges define between them a recess 14.

Although mouth shapes and sizes vary considerably, a one-size workpiece is initially moulded to be of such size and shape as to be capable of deformation to conform with most mouths with minimal further fitting. The material used in this embodiment is ethylene vinyl acetate copolymer, although other materials may be used. The device is positioned within the mouth while flanges 11 and 13 are hot (between 40° and 60° C.). The jaw is closed to press the teeth 16 of the upper arch into the recess 14 and the fingers are used to mould flange 11 and to mould flange 13 to conform to the mouth and thereby form the recess into a series of pockets 17, and the device while still hot is removed from the mouth and plunged into cold water so as to retain its shape. The lower flange 12 is then also heated and moulded to the mouth shape in front of the teeth of the lower arch, in the same manner.

When the device is applied, the upper flange 11 lies in an upper recess 20 (upper labial sulcus) (FIG. 6) which exists between the upper lips 21 and the upper gum 22, and the lower flange 12 will lie within the lower recess (lower labial sulcus) 23 within the mouth between the lower lip 24 and the lower gum 25. The inner flange 13 will lie against the back of the upper teeth 16 and the lower flange 12 against the front of the teeth 26 of the lower arch. The user's tongue will normally bear against the inner surfaces of the lower teeth 26 or the inner flange 13. The flanges are trimmed, if necessary, to avoid interference with the interior of a user's mouth.

Upon a breath being taken by a wearer, the lower lip 24 will normally be relaxed and will form a seal against the front face of the lower flange 12, even when the lower jaw drops during sleep. However, the lower lip 21 will move outwardly upon exhalation so that exhalation will not be inhibited by the device. As shown in FIG. 6, the depth of the flange 12 is less than the depth of recess 23. Even in sleep, a user by involuntary movement of the lower jaw, will under most circumstances open the mouth sufficiently to establish an air flow path past the flange 12, if he is in need of additional oxygen.

Because of the retention of the upper and lower flanges in their respective recesses within the mouth, and the intimate engagement of the surfaces defining the recess 14 by the surfaces within the mouth, there will be very little tendency for dislodgement of the device. The flanges 11 and 12 are thin and flexible and flange 13 does not occupy an excessive amount of the intra-oral space. Therefore the device is comfortable to use. It does not require any external parts, nor any aperture to receive the tongue. The invention can be applied inexpensively, and use can be made of other materials known to have characteristics similar to the ethylene vinyl acetate copolymer. Although the device may be applied "upside down" in certain instances, in most instances it is best used as described herein, with the teeth 17 of the upper arch engaged in recess 14 between inner flange 13 and outer flange 11.

I claim:

1. A snore inhibiting oral device comprising an imperforate, heat deformable, unitary moulding which comprises means for normally obstructing air passage through the mouth of a user causing the flow of air to the lungs of the user to pass solely through the user's nose yet allowing additional air passage through the mouth upon wide opening of the user's mouth, said obstruction means including means for defining a recess for receiving the teeth of the user's upper arch and for engaging front and rear surfaces of the teeth of the user's upper arch and means for lying in the recess between the teeth of the user's lower arch and adjacent lip of the user, said defining means comprising a first two flanges including an upper, inner flange and an upper, outer flange defining a space therebetween, said lying means comprising a third flange including a lower outer flange being of predetermined depth for extending into the lower recess of the user's mouth without extending the entire depth of the recess, said moulding further comprising, in plan, a general "U" shape and in cross-section, a general "Y" shape defined by said three flanges.

2. A snore inhibiting oral device according to claim 1 wherein said space between the inner and outer flanges contains a plurality of socket surfaces.

3. A snore inhibiting oral device according to claim 1 wherein the heat deformable moulding is formed of ethylene vinyl acetate copolymer.

4. A snore inhibiting oral device according to claim 3 wherein the flanges are thin and flexible.

* * * * *